United States Patent [19]

Sugiyama et al.

[11] 4,036,796
[45] July 19, 1977

[54] PROCESS OF DRYING AND HARDENING FILM-FORMING MATERIAL

[75] Inventors: Iwakichi Sugiyama, Narashino; Yukihisa Takaoka, Ibaraki; Kiyoshi Endo, Chiba, all of Japan

[73] Assignee: Matsumoto Seiyaku Kogyo Kabushiki Kaisha, Ichikawa, Japan

[21] Appl. No.: 545,314

[22] Filed: Jan. 29, 1975

[30] Foreign Application Priority Data

Jan. 29, 1974 Japan ............................ 49-12058

[51] Int. Cl.² ........................ C08L 91/00; C09F 9/00
[52] U.S. Cl. .............................. 260/22 CA; 106/264; 106/310; 260/22 A; 260/429.3
[58] Field of Search .............. 106/264, 243, 310; 260/429.3, 414, 18, 22 CA, 22 A

[56] References Cited

U.S. PATENT DOCUMENTS

| 2,681,922 | 6/1954 | Balthis | 260/429.3 |
| 2,739,902 | 3/1956 | Mack et al. | 106/264 |
| 3,461,146 | 8/1969 | Turner | 260/429.3 |

OTHER PUBLICATIONS

Chem. Abstract 65:13951a.

Primary Examiner—Theodore Morris

[57] ABSTRACT

When a film-forming material is dried and hardened in the presence of an alkoxy radical-containing zirconium compound-cobalt carboxylate complex, the drying process and hardness of the resulting film are improved.

9 Claims, 2 Drawing Figures

PROCESS OF DRYING AND HARDENING FILM-FORMING MATERIAL

BACKGROUND OF THE INVENTION

The present invention relates to a process for rapidly drying and hardening a film-forming material.

Heretofore, in the drying and hardening of a film-forming material from which a film can be formed by oxidation drying, a catalyst which comprises a major proportion of a lead soap and a minor proportion of one or more metallic soaps selected from the group consisting of cobalt, manganese, zinc, calcuim and zirconium soaps has been used. Among these dryers, the lead soap is particularly excellent in both internal drying property and surfaces drying property. However, this material is designated as a harmful metal and its discharge is severely limited. Also, lead and its compounds are regulated in their use as an additive for paints and varnishes.

Therefore, there has been a need for development of a lead-free dryer possessing the same effect as the lead dryer or a system including the same. For example, U.S. Pat. No. 2,739,905 has proposed the use of a zirconyl soap and U.S. Pat. No. 2,739,902 has proposed the use of a zirconyl soap in conjunction with a cobalt soap or a manganese soap. Also, the use of phenanthrolines in conjunction with a manganese soap has been proposed in U.S. Pat. Nos. 2,526,718 and 2,565,897. In addition, a dryer comprising zirconium and cobalt combined with each other through oxygen is disclosed in "Paint Technology", 35, (8), pages 18 to 19. Further, in Japan, a zirconium dryer is disclosed in "Toso Gijutsu (Painting Technique)", Dec., 1972, pages 86 to 87. These dryers all use a zirconium soap and are reported to have a catalytic performance superior to that of the prior cobalt soap alone. However, when these dryers are carefully examined, it is found that the surface drying and internal drying properties are not as good as lead containing dryers.

In earlier years, one of the applicants found that one type of a stabilized coordination compound formed by the coordination of a metallic soap such as a cobalt or manganese soap with a titanic acid ester such as titanium tetraisopropoxide and titanium tetra-n-butoxide exhibited excellent performance as a dryer for an oxidation polymerization driable film-forming material and obtained a patent therefor (reference is made to Japanese Pat. No. 604964). However, the titanic acid ester usually is highly reactive and reacts with water or functional groups contained in the film forming material, such as a hydroxyl group, carboxyl group, epoxy group, acetate group and the like to cause gelation in a short period of time, whereby it often becomes practicably useless and loses its economic value.

As a result of our study directed toward development of an excellent drying hardener for a film which is free from lead, we have found that a complex formed from an alkoxy radical containing zirconium compound and a cobalt carboxylate is very useful as a drying promotor for an oxidation polymerization driable film-forming material. This finding is a basis of this invention.

SUMMARY OF THE INVENTION

According to this invention, briefly summarized, there is provided a process for drying and hardening a film-forming material in which the drying and hardening are carried out in the presence of an alkoxy radical containing zirconium compound-cobalt carboxylate complex.

It is known that when the alkoxy radical containing zirconium compound (hereinafter referred to as an zirconium alkoxide for brevity) is added to a film-forming material, it reacts with the material to form a cross linking as the above-described titanic acid ester does. However, because of the tetravalent eight coordination of zirconium in comparison to the tetravalent six coordination of titanium, the zirconium alkoxide is highly reactive. For this reason, it has been impossible to date to add it to a film-forming material containing the above-described functional groups, and, in fact, the zirconium alkoxide itself has not been expected to have a function as a dryer as the metallic soaps do.

However, a zirconium alkoxide having a higher coordination ability than titanium is generally highly reactive with the metallic soaps conventionally used as a dryer, such as cobalt, zinc and iron naphthenates and octoates. For example, when cobalt octoate and zirconium tetra-n-butoxide are reacted, and the relationship between mole ratio and electrical conductivity during the reaction is examined by Job's method of continuous variation, it is observed that the curve of the electrical conductivity of the reaction system has a clear inflection point at a Co to Zr mole ratio of about 2 : 1. This inflection point indicates the formation of a complex having a ratio of the zirconium alkoxide to the cobalt carboxylate of 1 to 2.

On the other hand, when a titanic acid ester - cobalt soap system and a zirconium soap - cobalt soap or manganese soap system described in the above mentioned patent were determined for electrical conductivity under the same conditions, a clear indication of complex formation could not be confirmed as was the case with the zirconium alkoxide.

The complex formed by the reaction between the zirconium alkoxide and the cobalt carboxylate is very stable and causes no gelation or considerable change in viscosity of a film-forming material due to the action of the zirconium tetra-n-butoxide. It may be safely added to a film-forming material containing functional groups such as hydroxyl group, carboxyl group, epoxy group and acetate group and may be expected to act as a cross linking agent under appropriate conditions, and, at the same time, when it is added to an oxidation polymerization driable film-forming material, it exhibits a better dryer effect than the conventional cobalt soap, cobalt soap-zirconium soap system and lead soap-cobalt soap system. This complex exhibits an effect superior to that of the method described in U.S. Pat. No. 2,739,902 and other methods including the use of a zirconium soap or its compounds and is superior in tack-free drying property, internal drying property, hardness developing property, and final hardness to the conventional lead soap-cobalt soap system. It further provides a film excellent in water resistance, solvent resistance and adhesivity.

DETAILED DESCRIPTION

Figure 1:
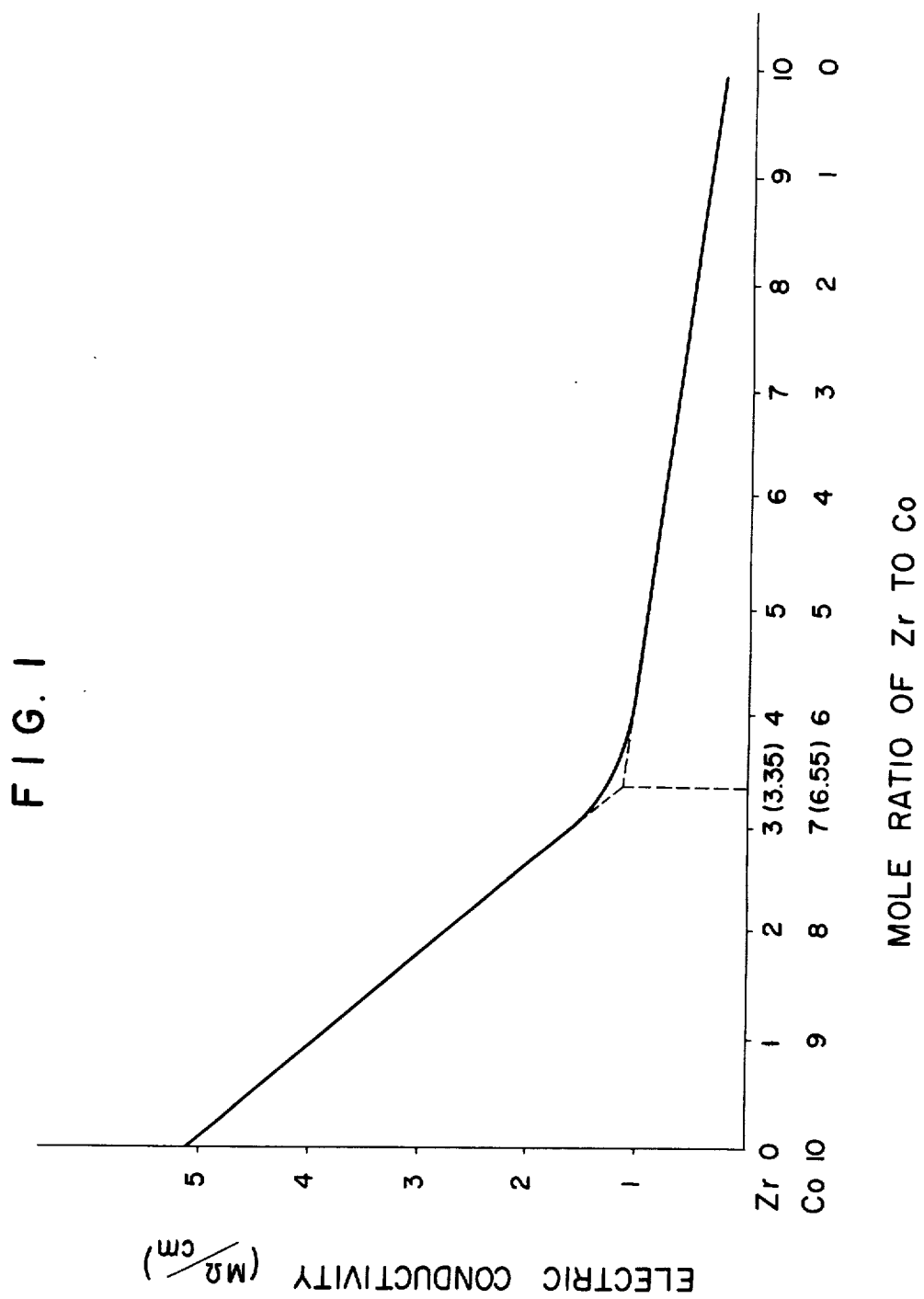
FIG. 1 is a graph showing the relationship between the electrical conductivity of an isopropanol solution of the reaction product between zirconium tetra-n-butoxide and cobalt octoate prepared in Preparation Example 1 and a mole ratio of Zr to Co.

The term "film-forming material" as used herein denotes a material capable of drying and hardening by oxidation polymerization thereby to form a film. A material capable of forming the primary or secondary bond (coordination bond or chelate bond) with zirconium alkoxide to provide a cross linkage is especially preferred. Examples of such a material are linseed oil modified alkyds, soybean oil modified alkyds, dehydrated castor oil modified alkyds, epoxy acrylate and unsaturated polyesters.

The term "zirconium alkoxide" as used herein denotes a zirconium tetraalkoxide of the formula

wherein R denotes an alkyl radical having from 2 to 10 carbon atoms, preferably 3 to 8 carbon atoms, and may be of the same kind or of different kinds, or a zirconium alkoxychelate compounds of the formula

wherein R denotes the same radical as described above, each of $m$ and $n$ is an integer of 1 to 3, $m$ plus $n$ equaling 4, and L denotes a $\beta$-diketone chelating ligand such as acetylacetone and benzoylacetone, the residue of a carboxylic compound containing a carbonyl group or hydroxyl group such as methyl acetoacetate, ethyl acetoacetate, ethyl salicylate, and ethyl lactate.

Examples of the zirconium tetraalkoxide are zirconium tetraisopropoxide, zirconium tetra-n-butoxide, zirconium tetraoctoxide and zirconium tetrahexoxide. Furthermore, examples of the zirconium alkoxychelate compounds are bis (acetylacetonato) zirconium di-n-butoxide, bis (acetylacetonato) zirconium dioctoxide, bis (methyl acetoacetate) zirconium diisopropoxide, and bis (ethyl lactate) zirconium di-n-butoxide. In addition, similar results can be obtained with the use of a zirconium compound wherein one or more of the R in the respective formula described above are a hydrocarbon residue such as alkenyl, allyl, cycloalkyl radical, and the like.

The cobalt carboxylate usable for the process of the present invention includes cobalt naphthenate, cobalt octoate and cobalt oleate.

In preparing a complex from the reaction between the zirconium alkoxide and the cobalt carboxylate, the two compounds are reacted together either in the absence or presence of an organic solvent inert to the both compounds, such as mineral spirit, toluene, xylene, chlorobenzene, alcohols, cellosolves, and the like at room temperature or elevated temperatures. As will be clearly seen from the measurement of electrical conductivity, the mole ratio of the zirconium compound of the cobalt compound in the reaction system especially preferably is 1 : 2 in terms of zirconium to cobalt (Zr/Co). Since it is possible to vary the mole ratio at will in the reaction depending on the content of the complex required, the ratio is not particularly limited. The complex thus obtained, wherein the ratio of Zr to Co is 1 : 2, has colors ranging from red purple to blue violet and is highly soluble in an organic solvent.

In the practice of the process of the present invention, the above-described complex may be added in an amount of 0.001 to 1% by weight, preferably 0.01 to 0.5% by weight, calculated in terms of a metal (Zr + Co) content, with respect to the film forming material. In this case, any other metallic soap such as calcium, manganese and iron soaps, amines and peroxides may also be used in conjunction with the complex.

Although the function and mechanism of the complex according to the present invention are not completely clear, it is considered that the cobalt carboxylate coordinates with the alkoxy-containing zirconium compound to provide a change in electron configuration in the both compounds, whereby the catalytic activity of the complex is enhanced, from a comparative examination of A.C. Zettlemoyer's interpretation that the catalytic performance of a manganese soap is remarkably enhanced by the coordination of amines around the soap due to the change in its electron configuration ("Industrial and Engineering Chemistry", vol. 46, (10), page 2220, 1954). Whatever the reason may be, in accordance with the present invention, there is provided a film-forming composition which is not inferior in performance to one containing a lead compound without using a harmful compound liable to cause environmental pollution and health hazards. Thus, the present invention is considered to have high utility for industrial purposes.

In order to indicate more fully the nature and utility of this invention, the following specific examples of practice are set forth, it being understood that these samples are presented as illustrative only and that they are not intended to limit the scope of the invention.

In the following examples, all parts and percentages are by weight.

Preparation of Example 1

Zirconium tetra-n-butoxide and cobalt octoate were respectively dissolved in a concentration of 0.0548 mole/100 ml in dehydrated and purified isopropanol. The resulting two solutions were mixed together in a ratio such that mole ratio of Zr to Co was 1/9, 2/8, 3/7, 4/6, 5/5, 6/4, 7/3, 8/2 and 9/1, for the resulting mixture was reacted under reflux of the isopropanol for 15 minutes and allowed to cool. The electric conductivities of the solutions thus obtained were measured. The results are shown in FIG. 1.

It is apparent from FIG. 1 that the curve of the electric conductivity has an inflection point in the neighbourhood of a ratio of Zr/Co of 3.35/6.55 (= 1/2). The resistance value at this point was 1.10 $\mu\Omega$/cm at a temperature of 20° C. Therefore, it was confirmed by Job's method of continuous variation that the two reaction components formed a complex of a Zr/Co mole ratio of 1 : 2.

Preparation Example 2

Zirconium tetra-n-butoxide and cobalt octoate were respectively dissolved in dehydrated and purified isopropanol in a concentration of 0.0548 mole/100 ml in the same manner as Preparation Example 1. The resulting two solutions were mixed together in a ratio such that the mole ratio of Zr/Co was 1/2. The resulting mixture was reacted under reflux of the isopropanol for 15 minutes, and the electrical conductivity of the reaction mixture was determined and found to be 1.15$\mu\Omega$/cm, which indicated the formation of a complex of a Zr/Co ratio of 1/2. The resulting solution was treated under vacuum to remove the isopropanol. A red purple, waxy solid was obtained.

This solid product is soluble in benzene, toluene, xylene, mineral spirit, ethanol, isopropanol and the like.

Figure 2:
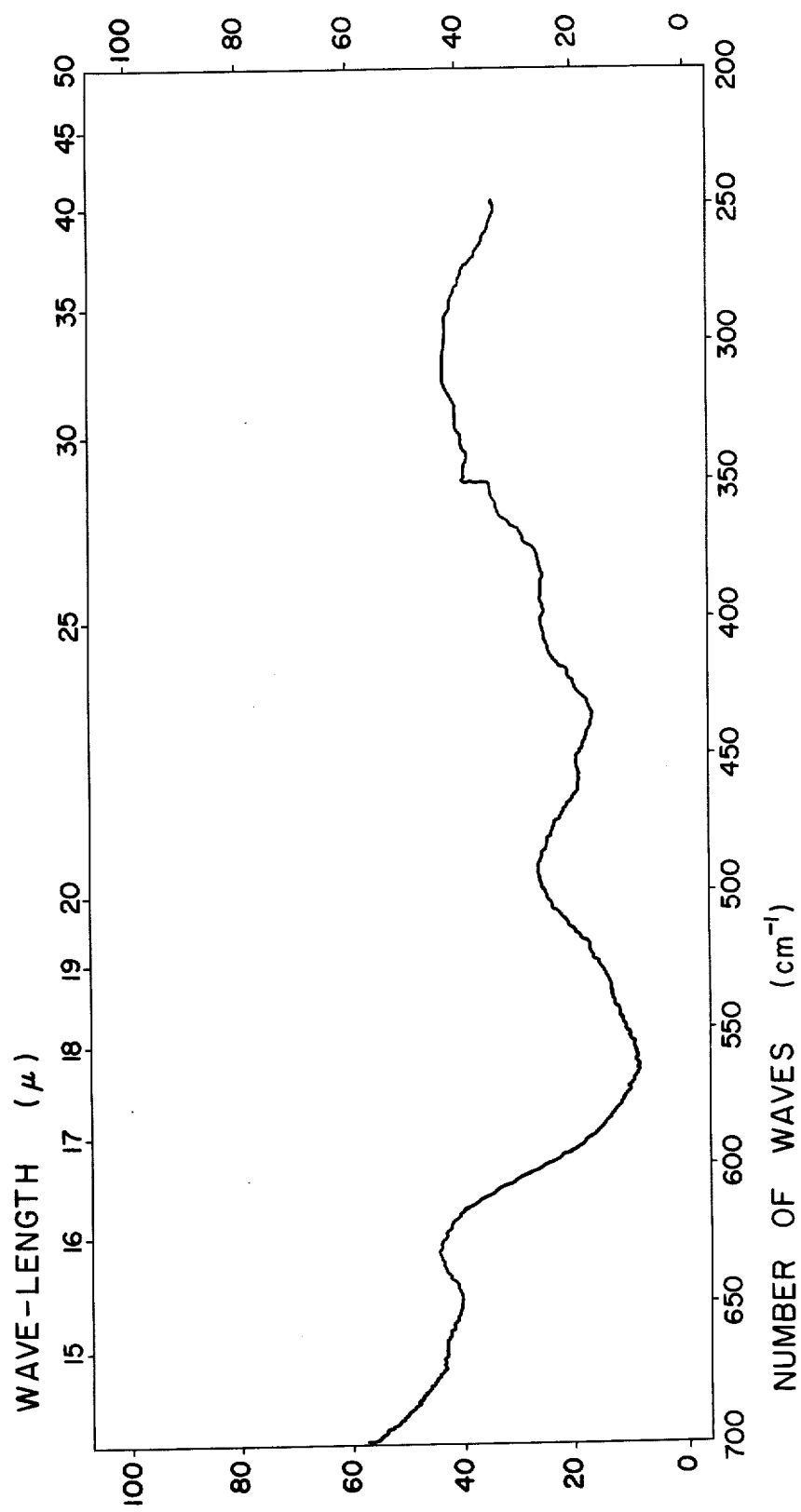
FIG. 2 is a graph showing a far infrared spectrum of an isopropanol solution of the reaction product of zirconium tetra-n-butoxide and cobalt octoate prepared in Preparation Example 2.

The far infrared absorption spectrum curve for a solution of the solid product in isopropanol is shown in FIG. 2.

Reference Example 1

With the procedure described in Preparation Example 1, zirconyl octoate and cobalt octoate was reacted together, and the electrical conductivity of the resulting reaction mixture was measured. No inflection point indicating the formation of a complex was observed.

Preparation Example 3

Di-n-butoxyzirconium bis (acetylacetonato) and cobalt naphthenate was respectively dissolved in dehydrated and purified isopropanol in a concentration of 0.0552 mole/100 ml. The resulting two solutions were mixed in such a manner that the mole ratio of Zr/Co was equal to the ratio described in Preparation Example 1. The resulting mixture was reacted under reflux of the isopropanol for 15 minutes and allowed to cool.

The determination of the electrical conductivity of the solution thus obtained indicated an inflection point in the neighbourhood of a Zr/Co ratio of 3.40/6.60 = 1/2. The resistance value at this point was 1.25 $\mu\Omega/cm^2$ at a temperature of 20° C. The result of Job's method of continuous variation indicated that the Zr-Co reaction system formed a complex of Zr/Co mole ratio of 1 : 2.

Preparation Example 4

Dibutoxyzirconium bis (acetylacetonato) and cobalt naphthenate were respectively dissolved in dehydrated and purified isopropanol in a concentration of 0.05 mole/100 ml in the same manner as in Preparation Example 3. The resulting two solution were mixed together in a ratio such that a Zr/Co mole ratio was 1/2. The resulting mixture was reacted under reflux of the isopropanol for 15 minutes and allowed to cool.

The electrical conductivity of the reaction mixture thus obtained was measured and found to be 1.23 $\mu\Omega$/cm. The solution was treated under a reduced pressure of 10 mm Hg to remove the isopropanol, whereupon a red purple waxy solid product was obtained. The product, similar to that in Preparation Example 2, was soluble in benzene, toluene, xylene, mineral spirit, isopropanol, and the like.

Reference Example 2

With the procedure described in Preparation Example 3, zirconium octoate and cobalt naphthenate were reacted together, and the electrical conductivity of the resulting reaction mixture was determined. The result indicated no inflection point, which indicates that no complex was formed.

Examples 1 to 2

In each of Examples 1 to 2, the complexes obtained in Preparation Examples 2 and 4 in the quantities indicated in Table 1 were respectively added to a reagent grade soybean oil (of iodine value of 123 and oxidation number of 0.28) to produce homogeneous solutions. The resulting solutions were respectively applied onto a glass plate to a thickness of 3 mils by means of a doctor blade. The tack-free drying times of these coated glass plates were determined in an atmosphere at a temperature of 25° C and a relative humidity of 70%. The results are shown in Table 1.

As Comparative Examples, film-forming compositions were prepared by using the procedure described above except that known hardeners as indicated in Table 1 were used instead of the present complex. The test results of these Comparative Examples are also shown in Table 1.

Table 1

| | Hardener Type | Quantity (%, as metal) | Drying time (minute) |
|---|---|---|---|
| Example 1 | Complex of Preparation Example 2 | 0.23 | 210 |
| Example 2 | Complex of Preparation Example 4 | 0.23 | 220 |
| Comparative Example 1 | Pb - octoate / Co - octoate | 0.25 / 0.05 | 340 |
| Comparative Example 2 | Pb - octoate / Zr - octoate | 0.25 / 0.10 | 310 |
| Comparative Example 3 | Co - octoate / Zr - octoate | 0.25 / 0.10 | 300 |
| Comparative Example 4 | Mn - octoate / Phenanthroline | 0.25 / 0.10 | 300 |

It is apparent from Table 1 that the process of the present invention provided a better drying property.

Examples 3 and 4

The complexes obtained from Preparation Examples 2 and 4 were respectively added to a 50% solution of a soybean oil modified medium oil type alkyd resin (oil length 55%) in mineral spirit in the quantities indicated in Table 2, and the resulting solutions were respectively applied onto a glass plate in the same manner as in Examples 1 and 2. These coatings were tested for drying property, film hardness and solvent resistance (residue of toluene). The results are shown in Table 2.

As Comparative Examples, film-forming compositions were prepared and tested using the same procedures as described above except that known hardeners as indicated in Table 2 were used in place of the present complex. The test results of these Comparative Examples are also shown in Table 2.

In Table 2, the internal drying means the time required to completely harden a film coating. The temperature and humidity conditions are the same as those set forth in Examples 1 and 2. The hardness was determined at a temperature of 18° C and a relative humidity of 70% by a Sward Rocker. The solvent resistance was determined as follows. The film formed was immersed in toluene for 2 hours and thereafter, it was removed from the toluene and dried at a temperature of 125° C. Then, the residue of the toluene in the dried film was calculated according to the following equation:

$$\text{Residue} = W_1/W_2 \times 100$$

wherein $W_1$ is the weight of the dried film, and $W_2$ is the weight of the film before immersion in toluene. The residue thus obtained indicates solvent resistance.

Table 2

| | Hardener | | Drying property (minute) | | | Hardness | | | Solvent resistance | |
|---|---|---|---|---|---|---|---|---|---|---|
| | Type | Quantity (% as metal) | Tack free drying | Hard-ening | Internal drying | After 1 day | After two days | After three days | After 1 day | After two days |
| Example 3 | Complex of Preparation Example 2 | 0.36 | 70 | 120 | 150 | 28 | 35 | 39 | 89.5 | 90.1 |
| Example 4 | Complex of Preparation Example 2 | 0.36 | 80 | 130 | 170 | 26 | 34 | 37 | 87.3 | 89.8 |
| Comparative Example 5 | Pb-naphthenate Co-naphthenate | 0.3 0.06 | 120 | 240 | 320 | 19 | 22 | 31 | 80.2 | 87.4 |
| Comparative Example 6 | Co-octoate Zr-octate | 0.1 0.3 | 120 | 260 | 340 | 17 | 20 | 29 | 79.3 | 84.5 |

As can be seen from Table 2, the films prepared according to the process of the present invention are remarkably good in both surface drying property and internal drying property and, further, have better hardness and solvent resistance than those obtained from the prior art process. The reason for such excellent results is that the complex according to the present invention not only functions as a drying agent, but also acts as a cross linking agent.

Example 5

To a base composition comprising 550 parts of a tall oil modified alkyd resin (oil length 60%), 10 parts of calcium carbonate, 20 parts of titanium white, 5 parts of zinc white, and 10 parts of mineral spirit was added the complex (mole ratio of Co/Zr of 2/1) prepared in Preparation Example 2 in a quantity of 0.39%, calculated in terms of the metal content, to produce a long oil type alkyd enamel.

The enamel was applied on a glass plate in the same manner as described in Examples 2 and 3, and the resulting film was subjected to the same drying test as that specified in Examples 3 and 4. Also, the enamel prepared as described above was spray-coated on a glass plate to a thickness of about 50 μ, and the resulting coating was tested for pencil hardness and Erichsen value at a temperature of 20° C and a relative humidity of 70%. The results are shown in Table 3.

For comparison purpose, another long oil type alkyd enamel was prepared from the same composition as described above except that Co - octoate - Pb - octoate, which has been heretofore considered to be the best hardener, was added in quantities of 0.42% (calculated in terms of metal) and at a ratio such as to provide a Co/Pb mole ratio of 1/6, instead of adding the complex from Preparation Example 2. With this alkyd enamel, the same tests as specified above were carried out. The results as shown in Table 3.

Table 3

| | Drying property (minute) | | Pencil hardness | | Erichsen Value |
|---|---|---|---|---|---|
| | Tack-free drying | Internal drying | After 2 days | After 10 days | After 2 days |
| Example 5 | 270 | 380 | 2B - B | F - H | 5.5 |
| Comparative Example 7 | 410 | 600 | 3B | HB - F | 5.5 |

From Table 3, it is apparent that the process of the present invention is superior to the process using the Pb - Co system.

Example 6

A film-forming composition comprising 100 parts of epoxy acrylate, 40 parts of 2-hydroxyethyl methacrylate, 2.5 parts of cumene hydroperoxide and a complex in the quantity indicated in Table 4, which complex was prepared in Preparation Example 2, was applied on a glass plate to a thickness of 4 mil, and the coated plate was treated at a temperature of 100° C. In this composition, the epoxy arcylate component was prepared by reacting 380 parts of a bisphenol type epoxy resin containing an epoxy equivalent of 192 with 172 parts of methacrylic acid, 0.2 part of triethylamine and 0.4 part of hydroquinone. The tack-free drying time of heated-treated film was determined. The result is shown in Table 4.

For comparison purpose, other film-forming compositions were prepared and tested by the same procedures as those described above except that known hardness as indicated in Table 4 were used in place of the present complex. The results of these Comparative Examples are also shown in Table 4.

In Table 4, the hardness represents pencil hardness. This pencil hardness was determined after the coated film which had been subjected to a tack-free drying was kept at a temperature of 100° C for a further 30 minutes and thereafter left at a temperature of 20° C and a relative humidity of 70% for an hour.

Table 4

| | Hardener | | Tack-free drying property (minute) | Hardness |
|---|---|---|---|---|
| | Type | Quantity (%, as metal) | | |
| Example 6 | Complex of Preparation Example 2 | 0.36 | 25 | H - 2H |
| Comparative Example 8 | Co-naphthenate | 0.4 | 120 | B - HB |
| Comparative Example 9 | Co-naphthenate Pb-naphthenate | 0.06 0.3 | 100 | F - HB |
| Control | — | — | >720 | — |

The results set forth in Table 4 clearly indicates that the process of the present invention provides a more rapid rate of hardening and a more sharp development of hardness than the conventional process.

Example 7

A small amount of hydroquinone was added to a mixture of 2.2 moles of propylene glycol, 1 mole of maleic anhydride, and 1 mole of phthalic anhydride, and the resulting mixture was reacted together to prepare a polyester resin. To 100 parts of the polyester resin was added 30 parts of styrene. 2% of methyl ethyl ketone and the complex from Preparation Example 4 in the quantity indicated in Table 5 were added to the resulting mixture, and the mixture thus obtained was dissolved to produce a homogeneous solution.

The resulting solution was applied onto a glass plate to a thickness of 4 mils, and the tack-free drying time of the coated film was determined at a temperature of 25°

C and a relative humidity of 71%. The result is shown in Table 5.

For comparison purposes, other film-forming compositions were prepared and tested by the same procedures as those described above except that known hardeners as indicated in Table 5 were used in place of the present complex. The results of these Comparative Examples are also shown in Table 5.

Table 5

|  | Hardener | | |
|---|---|---|---|
|  | Type | Quantity (% as metal) | Tack-free drying property (minute) |
| Example 7 | Complex of Preparation Example 4 | 0.45 | 25 |
| Comparative Example 10 | Co-naphthenate | 0.45 | 60 |
| Comparative Example 11 | Co-naphthenate | 0.15 | |
|  | Zr-octoate | 0.30 | 440 |

From Table 5, it is apparent that the process according to the present invention is superior in tack-free drying property to the conventional process.

We claim:

1. A process of drying and hardening a film-forming material which comprises using as a dryer for said film-forming material as alkoxy-radical containing zirconium compound-cobalt carboxylate complex, said alkoxy radical-containing zirconium compound being selected from the group consisting of zirconium tetraalkoxides of the formula:

$$Zr(OR)_4$$

wherein R denotes an alkyl radical having from 2 to 10 carbon atoms and may be of the same kind or of different kinds, and zirconium alkoxychelates of the formula:

$$Zr(L)_n(OR)_m$$

wherein R denotes the same radical as defined above, L denotes a chelating ligand selected from the group consisting of β-diketones, hydroxy esters, and ketoesters, and m and n are integers each of 1 to 3, m plus n equaling 4, the cobalt carboxylate being a member selected from the group consisting of cobalt salts carboxylic acid having from 6 to 18 carbon atoms, the mole ratio of cobalt to zirconium of said complex being of the order of 2 : 1.

2. The process according to claim 1 wherein the complex is used in a quantity of 0.001 to 1% by weight, calculated in terms of metal, based on the weight of said film-forming material.

3. The process according to claim 1 wherein the alkoxy radical-containing zirconium compound is zirconium tetra-n-butoxide.

4. The process according to claim 1 wherein the alkoxy radical-containing zirconium compound is di-n-butoxy zirconium bis (acetylacetonato).

5. The process according to claim 1 wherein the cobalt carboxylate is a member selected from the group consisting of cobalt naphthenate, cobalt octoate, and cobalt oleate.

6. The process according to claim 1 wherein the film-forming material is a material capable of drying and hardening by oxidation polymerization thereby to form a film.

7. The process according to claim 6 wherein the film forming material is a member selected from the group consisting of linseed oil modified alkyds, soybean oil modified alkyds, dehydrated castor oil modified alkyds, epoxy acrylate and unsaturated polyester.

8. The process according to claim 1 wherein the complex is previously prepared prior to being added to the film forming material.

9. The process according to claim 1 wherein the alkyl radical contains from 3 to 8 carbon atoms.

* * * * *